United States Patent [19]
Schuss

[11] 4,354,839
[45] Oct. 19, 1982

[54] DENTAL HANDPIECE

[76] Inventor: Werner Schuss, In der Lahrbach 18, 6148 Heppenheim, Fed. Rep. of Germany

[21] Appl. No.: 211,688

[22] Filed: Dec. 1, 1980

[30] Foreign Application Priority Data

Nov. 29, 1979 [EP] European Pat. Off. ........ 79104768.1

[51] Int. Cl.³ .................... A61C 1/08; A61C 17/02; A61C 1/12
[52] U.S. Cl. ...................................... 433/126; 433/82
[58] Field of Search .................. 433/114, 133, 82, 85

[56] References Cited

U.S. PATENT DOCUMENTS

| | | | |
|---|---|---|---|
| 3,229,369 | 1/1966 | Hoffmeister et al. | 433/133 |
| 4,198,755 | 4/1980 | Landgraf | 433/126 |
| 4,217,101 | 8/1980 | Loge | 433/126 |
| 4,251,212 | 2/1981 | Worschischek et al. | |
| 4,278,428 | 7/1981 | Straihammer et al. | 433/126 |

FOREIGN PATENT DOCUMENTS 2908390 9/1979 Fed. Rep. of Germany .

Primary Examiner—Robert Peshock
Attorney, Agent, or Firm—Hill, Van Santen, Steadman, Chiara & Simpson

[57] ABSTRACT

A dental handpiece which has a drive transmission for transmitting the rotation from a motor to a socket receiving a tool for rotation in the head of the handpiece and having at least one cooling agent line formed in sections with two of the sections being connected to one another by a rotatable connection characterized by a first drive shaft having a direct coupling with the drive shaft of the drive part at one end and having two coaxially arranged gears of different number of teeth disposed on the other end, a first sleeve supporting the first drive shaft and having each cooling line section terminating in an annular groove forming part of the rotatable connection, a second sleeve telescopically received on the first sleeve and having each cooling line section starting with a radially extending port for communicating with an annular groove, a first releasable connection between the first sleeve and the housing of the drive part which does not allow any rotation therebetween, a second releasable connection between the first sleeve and second allowing rotational movement without axial displacement, a grip part formed by the first, second sleeves and an outer sleeve covering which receives a neck portion of the head part and supports a second drive shaft having a gear at each end and mountable so that either the gear at one end is engaged with one of the two gears of the first drive shaft or the gear at the opposite end is engaged with the other of the two gears to enable a different gear ratio between the first and second drive shafts.

8 Claims, 6 Drawing Figures

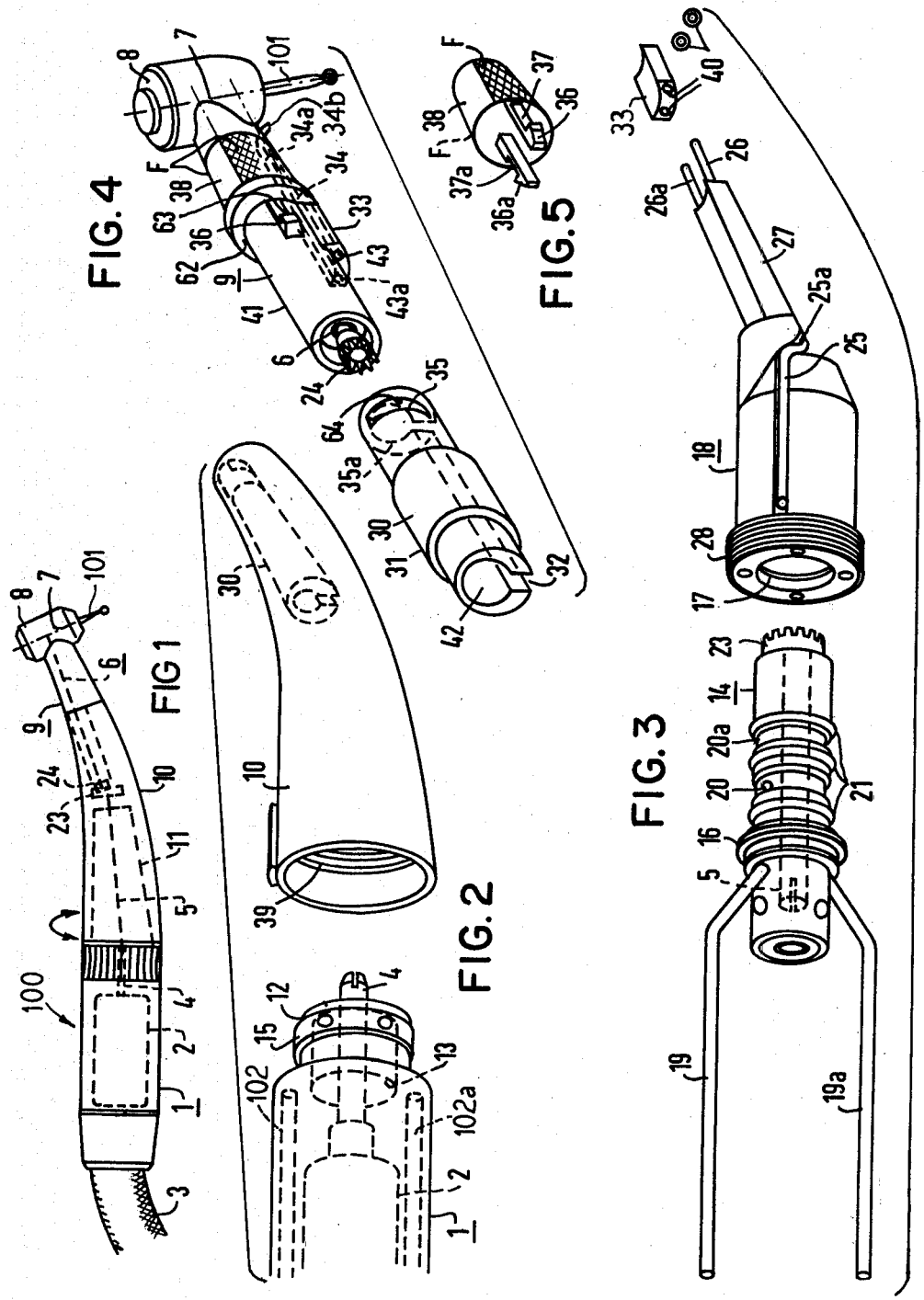

DENTAL HANDPIECE

BACKGROUND OF THE INVENTION

The invention is directed to a dental handpiece which has a drive transmission including a first and second drive shaft section for transmitting rotational motion from a drive motor to an acceptance sleeve or chuck which rotatably supports a dental tool in the head housing of the handpiece. In order to obtain a different drive relation, the first drive shaft has a pair of coaxially arranged gears of different number of teeth and the second drive shaft can be mounted so a gear on its end will engage a selected one of the two gears to enable changing the drive ratio. In addition, the handpiece has cooling agent lines or segments with at least two line segments in the grip section being connected together by a rotatable coupling consisting of an annular channel or groove in one of the members cooperating with a radially extending port and the other member when the two members are telescopically assembled together with sealing rings adjacent the channels to enable rotation between the members which are held to be free of any axial displacement.

In known dental handpieces, the handle or grip section in the head part forms a so-called grip part or angle which can be rotated with respect to the drive part and can be releasably removed from the drive part. From this end, the drive end contains a guide shank or projection which surrounds the drive shaft. The guide shank or projection is engaged in a corresponding bore in the grip part until the gear of the drive shaft is engaged with a drive shaft section of the corresponding grip part. In this position, the handpiece is secured against axial slippage by means of a catch device which is operationally releasable and essentially consists of a snap ring groove in one of the parts and a catch spring carried by the other part and radially engaged in the ring groove to form the coupling or connection therebetween.

This type of coupling enables relative rotation between the drive part and the grip part or section and when cooling agent transmission lines are internally provided in the handpiece, the coupling must provide a rotational coupling for the two cooling line sections. Such a rotational coupling comprises a cooling line in one of the parts such as the motor part terminating in an angular groove on the projection and the grip part having radial ports extending into the cooling lines contained therein which radial ports are in communication with the annular groove when the two parts are assembled together. To insure sealing between the two parts, sealing members such as O-rings are provided adjacent the annular grooves.

In order for the handpiece to be operative at different speed ranges, a plurality of handpiece units consisting of head parts, neck parts and grip pieces are made available with each of these units having a different step down or respectively step up in the gear ratio. Thus, by selecting one of these handpiece units and assembling it on the drive part, a desired step up or step down in the gear ratio can be obtained.

The use of different and complete handpiece units as mentioned above to obtain different drive speeds for the tool involves a relatively large cost in terms of both structure and pieces. This is because each handpiece unit consists of a head part with a head housing, a neck and a handle or grip piece or part. Another disadvantage is that the rotatable coupling if provided between the handpiece units and the drive part will be released and uncoupled during each of the transfers or changes in the handpiece unit. Such constant coupling and uncoupling of the rotatable connection increases a danger of dust or dirt penetrating into the various cooling line sections such as the annular channel and/or radial ports. The constant coupling and uncoupling also applies shear stresses on each of the sealing rings. The repair or servicing of the cooling lines, which may become necessary due to blockage thereof, can generally only be carried out in a work shop. Then the entire handpiece unit is not available to the dentist during these times of repair.

SUMMARY OF THE INVENTION

The present invention is directed to providing a dental handpiece which has a simplified construction and improvements with regard to the goals of achieving a reduction in the number of handpiece base parts and constructions necessary to enable providing the handpiece with a series of different gear ratios between the drive part and the rotatable socket. The invention also provides a dental handpiece whose parts, that are subject to wear and require maintenance, are of a relatively simple design and can be quickly replaced.

To accomplish these goals, the present invention is directed to an improvement in a dental handpiece having a drive part with a drive shaft extending in a projection, a head part with a head housing containing socket means for supporting a tool for rotation and having a neck extending therefrom and a grip part connected to the head part and being removably supported on the projection of the drive part so that it can be axially removed therefrom, said grip part having drive means for transmitting rotational motion from the drive shaft of the drive part to the socket means, said handpiece having at least one cooling agent line formed of sections in said parts with two of said cooling line sections being connected to one another by means of a rotatable connection consisting of an annular channel in one of said parts with annular sealing rings and an opening in the other of said parts in commmunication with said channel in said other part and being rotatable therearound. The improvement comprises a first drive shaft having means at one end to form a direct coupling with the drive shaft of the drive part and having two coaxially arranged gears of a different number of teeth disposed on the other end, said first drive shaft being supported for rotation in a first sleeve which forms one of the two parts of the rotatable connection and carries one of the cooling line sections, a second sleeve forming the other part of the rotatable connection being arranged concentrically on the first sleeve and having a cooling line section for conducting fluid from said connection to the head section, said first sleeve having first means coacting with the drive part for detachable connecting the first sleeve on said drive part without any rotation therebetween, said first sleeve and second sleeve having second means for releasably securing the second sleeve concentrically on the first sleeve for rotation thereon without any axial displacement, said grip part being formed by said first sleeve, said second sleeve and an outer sleeve covering supported thereon, said sleeve covering having means for receiving the neck of the housing of the head part, said neck having support means for supporting a second drive shaft having a gear at each end, said support means supporting the second drive shaft with a gear of one end being engaged with one of the two concentric gears of the first drive shaft section, so that by replacing the head part with another head part having the drive shaft supported with the gears engaged with the other of said two coaxial gears enables changing the gear ratio between the connection of the first drive shaft and the drive shaft of the head part.

A significant advantage of the dental handpiece in accordance with the present invention is that the complete handpiece up to the guide shank or projection of the drive part need no longer be interchanged in order to be able to work at different speed arrangements. In the handpiece of the present invention, only the head part with the head housing and the neck which is connected thereto need be interchanged in order to obtain a change in the drive speed. Thus, the present invention has few duplicated parts and provides a dental handpiece which can have its drive ratio changed with fewer and cheaper parts.

The first means coacting with the drive part for detachably connecting the first sleeve on the drive part preferably includes at least one recess on an outer surface of the first sleeve, a ball for each of said recesses, a radial bore in said projection of said drive part for each ball, and means for holding said ball in its bore against said recess to form the detachable connection between the first sleeve and the drive part.

Preferably, the second means for releasably securing the second sleeve concentrically on the first sleeve for rotation therewith without any axial displacement includes a resilient ring carried on said first sleeve and an annular groove in said second sleeve. The means for holding said ball of said first means includes means for holding said resilient ring in a retracted position to enable assembly of the second sleeve on the first sleeve. Preferably, the means for holding comprise a ring member telescopically received on said projection and having a first groove for the balls and a second axially spaced groove for engaging said resilient ring as the ring member is displaced onto the first sleeve.

BRIEF DESCRIPTION OF THE DRAWINGS

FIG. 1 is a side view of a dental handpiece in accordance with the present invention;

FIG. 2 is a partial exploded perspective view of the dental handpiece of FIG. 1;

FIG. 3 is a partial exploded perspective of internal parts of the dental handpiece of FIG. 1;

FIG. 4 is another partial exploded view of the head portion and internal parts of the handpiece;

FIG. 5 is a perspective view of a portion of the headpiece illustrated in FIG. 4.

DESCRIPTION OF THE PREFERRED EMBODIMENTS

Figure 6:
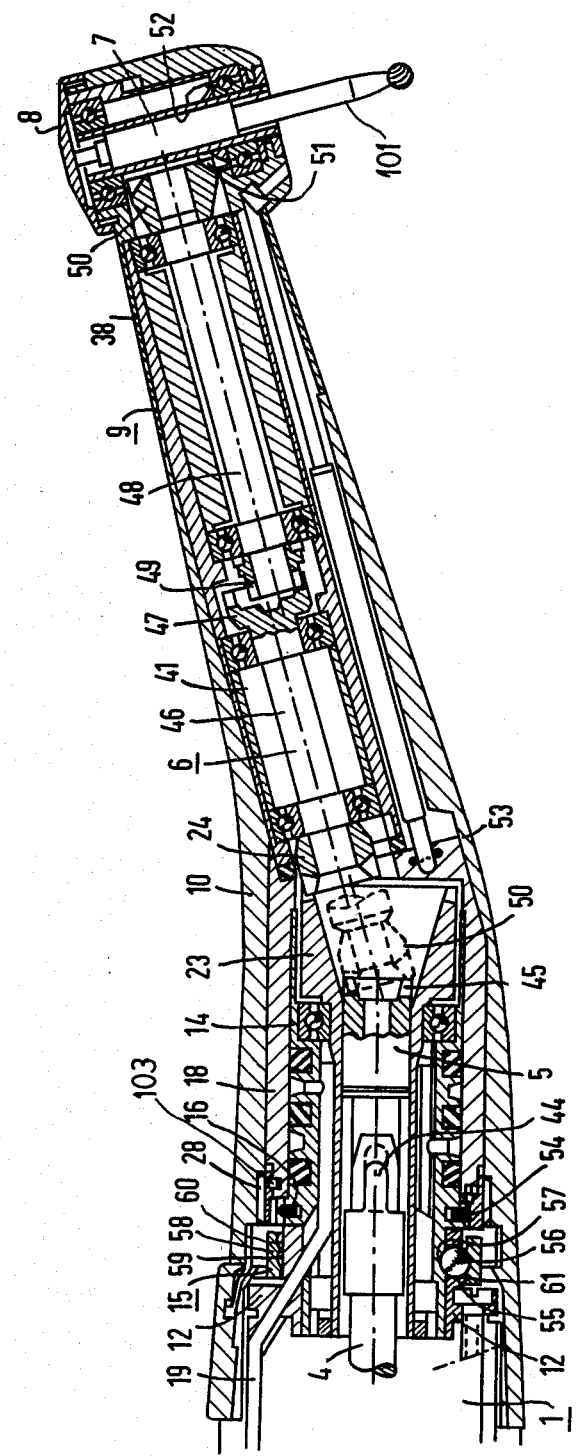
FIG. 6 is a longitudinal cross-section of a portion of the dental handpiece of FIG. 1.

The principles of the present invention are particularly useful in a dental handpiece generally indicated at 100 in FIG. 1.

The handpiece 100 is composed of a drive section or part 1, an angled portion or grip piece or part 10 and a head part or portion 9. The drive section or portion 1 contains a drive motor 2 for example an electric motor 2, which receives its drive energy from conductors in a supply hose 3 and has a drive shaft 4. In an angled portion 10, a drive train, which is composed of drive shafts 5 and 6, transfers rotational motion or output from the drive shaft 4 to a rotatable tool acceptance shaft or socket 7 that receives and supports a dental tool such as a drill 101 for rotation in a head housing 8 of the head part or headpiece 9. The head housing 8 is part of the head part 9 which accepts the two drive shaft sections 6 and 7 as well as their bearings and which is removably seated on a handpiece grip part 10 which is an angled portion. The part 10 encloses a bearing unit 11 which is formed of two concentric sleeves 14 and 18 (FIG. 3) that have bearing units for the drive shaft section 5 as well as the rotational connection for conveying one or more cooling agents from the drive part or section 1 to the head part or section 9. The handpiece grip part or portion 10 together with the head part 9 and the bearing unit 11, which will be described in greater detail below, will rotate with respect to the drive part 1 around the longitudinal axis of the handpiece which is the axis of the drive shaft 4.

The drive part 1 (FIG. 2) has a sleeve like or cylindrical shoulder or projection 12 surrounding a socket 13 indicated in broken lines through which the drive shaft 4 extends. The socket 13 receives one end of the sleeve 14 when the handpiece parts are assembled. On an outer surface of the shoulder or projection 12, a ball catch 15 is provided for axially securing the sleeve 14 in the socket 13. The sleeve 14, which is best illustrated in FIG. 3, contains a spring washer or resilient ring 16 which engages into a snap ring groove 17 of the sleeve 18 during assembly. Two cooling agent lines 19 and 19a are secured to the sleeve 14 and the ends of the cooling lines discharged in a known manner via radial bores or ports into annular channels 20 and 20a, which are sealed from one another by means of packing rings or ring seals such as O-rings 21. In addition the sleeve 14 also accepts and supports the first drive shaft 5 which has one end connected to the drive shaft 4 of the motor 2 and the opposite end supporting a bell-shaped drive gear 23 which will be engaged with the gear 24 (FIG. 4) on the drive shaft section 6. In the assembled state, the ends of the cooling lines sections 19 and 19a, which project from the sleeve 14, are engaged in slots in the projection 12 and in longitudinal grooves and/or bores 102, 102a of a drive housing of the drive part 1 and can be connected to supply lines which are arranged in the hose 3.

In an assembled state, the sleeve 18 (FIG. 3) is arranged concentric to the sleeve 14 and contains the coolant line sections 25 and 25a which have radial ports for receiving the coolant agent from the annular grooves 20 and 20a in a known manner. The coolant lines 25 and 25a terminate in tubular prongs 26 and 26a which are mounted in a diagonally extending portion or extension 27 of the sleeve 18. The sleeve 18 further contains a threaded ring 28, which is rotatably mounted on the sleeve 18 by a pin arrangement 104 (FIG. 6) and contains the snap ring groove 17 for engagement with the spring washer 16 when the sleeve 18 is assembled on the sleeve 14. The sleeve 18 is axially secured in the handpiece by means of the threaded ring 28 being threaded into threads 39 (FIG. 2) of a sleeve covering of the grip part 10.

The grip portion or part 10, as illustrated in FIG. 2, adjacent the head 9 receives a resilient slotted guide bushing 30. As best illustrated in FIG. 4, the bushing 30 has a collar 31 which is snapped into a socket of the grip portion 10. The guide bushing 30 is thus secured in the handpiece portion 10 against axial slippage. As illustrated, the guide bushing 30 is provided with cylindrical bore 42 and a continuous longitudinal slot 32 which receives the projecting portion 27 of the sleeve 18 and also a longitudinal fitting strip or member 33 of the head part 9. As illustrated, the strip 33 of the head part 9 contains cooling agent line sections 34 and 34a which discharge into a common cooling agent discharged nozzle 34b in the area of the tool 101 supported in the head 8.

The guide bushing 30 serves to prevent twisting of the part 18 relative to the part 9 and also contains two circumferentially spaced catch slots 35 and 35a which are shown as being on both sides of the bushing. The slots 35 and 35a receive radial resilient catch noses or dogs 36 and 36a when the head part 9 is axially assembled onto the grip section or portion 10. The two catch noses 36 and 36a are secured on a springlike tubular sleeve 38 (FIG. 5) by means of bridges 37 and 37a which extend parallel to the axis of the sleeve. The spring sleeve 38 is designed with a very thin wall and is arranged on the head part 9 in such a manner that it forms an outer generated surface. By means of radial pressure against the sleeve 38 for example by using the thumb and index finger, the two catch noses 36 and 36a can be moved radially towards the inside and therefore will be released or disengaged from the slots 35 and 35a.

The bridges 37 and 37a need not be absolutely rigidly arranged at the actuation sleeve 38. It is also conceivable within the framework of the invention for the head 9 to be connected to the grip portion 10 by a friction type lock for example by insertion in the guidance groove of the grip portion. Variations of the sample embodiment illustrated are also possible with respect to the number of catch noses provided without leaving the framework of the invention. The disposition of the two catch noses lying diametrically opposite one another, however, is particularly advantageous although it is also conceivable to provide only one catch nose or three or respectively four catch noses for specific purposes. An embodiment in which the resilient sleeve is provided with one or more recesses on a circumference and the bridges together with the catch noses are arranged on the member 30 is also within the framework of the present invention.

For assembling the handpiece, the bushing 30 is first clamped into the grip part 10. The collar 31 is thus engaged in the corresponding socket of a sleeve-like grip part 10 and prevents axial dislocation of the bushing. Subsequently, the sleeve 18 is inserted into the handpiece grip part 10 with the projection 27 engaged in the longitudinal slot 32 of the guide bushing 30. By means of the threaded ring 28, which is rotatably mounted on the sleeve 18, the sleeve 18 is axially fixed within the handpiece portion 10 as the threads of the ring 28 are received in the internal threads 39. The sleeve 14 as already mentioned is connected in a twist proof but axially releasable manner on the drive part 1 by means of the ball catch device 15. The handpiece grip portion 10 with the guide bushing 30 is supported therein and the sleeve 18 with the cooling agent lines 25 and 25a can now be axially slipped onto the sleeve 14 until the spring washer 16 is received by the groove 17 and the two handpiece parts are then axially fixed or connected together.

The head part 9 in addition to including the spring like sleeve 38 has a tubular shank or neck part 41 with a portion of the fitting strip 33 extending from one side thereof. When the head part 9 is assembled with the grip portion 10, the shank 41 is received in the bore 42 of the bushing 30 and the strip 33 is received in a portion of the slot 32. Thus the head part 9 will be secured against twisting relative to the bushing 30 and to the sleeve 18. Prior to assembly, elastic seals 40 consisting of one or more elements are inserted over the prong-like projections 26 and 26a of the coolant lines 25 and 25a. Thus, during assembly the prongs 26 and 26a will be received in sockets 43 and 43a of the member 33 to complete the connection to the cooling agent line sections 34 and 34a. The amount of insertion of the shank into the bore 42 is limited by a shoulder 62 but not until after the catch noses 36 and 36a have been engaged in the catch slots 35 and 35a so that the head part 9 is first axially fixed with respect to the grip portion 10. In the catch position, the seals guarantee a tight connection between the cooling line sections 25 and 34.

In addition, the seals 40 also fulfill another function namely providing sufficient clearance between the two gears 23 and 24 for proper meshing engagement. To this end, the two catch noses 36 and 36a are engaged in the slots 35 and 35a with a slight axial play. The pre-stress force created by the seals 40 will bias the head part 9 away from the grip part 10. Thus, the desired clearance between the handpiece parts in the axial direction is obtained due to the detent of the edge 63 of the catch nose 36 and 36a being engaged tightly against the sides 64 of the slots 35 and 35a. Due to this arrangement, the shoulder 62 can be eliminated.

Instead of utilizing the elastic seals 40, a spring wire, a spring band or the like can be exerted at right angles to the cooling fluid line sections 34. These spring members can be provided to act on an end face of the fitting strip or member 33 or a part thereof to urge the head part 9 away from the gripping sleeve 10. This biasing ensures the axially effective pressure and spacing between the two gears 23 and 24 when the handpiece parts are properly connected.

For releasing the head part 9, the spring sleeve 38 is pressed slightly together in a radial direction in the surface areas F which are a knurled outer portion adjacent each of the catch noses 36 and 36a. By means of this pressing together, which is expediently accomplished by the thumb and index finger, the spring sleeve is deformed thereby moving the catch nose from an engagement in the respective slots. The arrangement of the catch connection in the area illustrated allows a safe connection and disconnection of the handpiece parts because the head part need be grasped particularly only at the side surfaces, which is the surface area which merges tangenty into the head housing 8.

The surface and the arrangement of the drive shaft sections is best illustrated in FIG. 6. The first drive shaft 5 is directly coupled to the drive shaft 4 of the motor 2 by a dog coupling 44. On the end opposite the dog coupling, the first drive shaft section contains two coaxially aligned drive gears with different numbers of teeth. This is mainly the drive gear 23, which is a bell gear and surrounds a crown gear 45 which is smaller in diameter and has its teeth axially displaced from the teeth of the gear 23. The second drive shaft 6, which is supported for rotation by bearings in the neck or shank 41 of the head part 9 is composed of a first drive shaft section 46 and a second drive shaft section 48. As illustrated, the first drive shaft section 46 on one end has the gear 24 and on the opposite end has a gear 47 and the second drive shaft section 48 has a gear 49 which is in meshing relationship with the gear 47 and on an opposite end has a gear 50. Each of the drive shaft sections 46 and 48 are supported in the shank 41 by bearings with their axes being parallel to each other. The gear pairings of the larger diameter gear 47, which is an inside tooth or internal spur gear, with the smaller diameter outside or external spur gear 49 creates a step-up in the drive ratio of 1:1.5 between the shafts 46 and 48. The gear 50 at the end of the drive shaft section 48 faces the head housing and is designed as a conical gear which engages a gear 51 on the drive shaft 7 which supports the acceptance sleeve or chuck 52 that accepts the rotary tool such as 101.

The two drive shaft sections 46 and 48 as seen in FIG. 6 are supported in the head part 9. Thus, in a narrow sense they are also components of the housing of the head part 9 in particular the shank portion 41. In the position illustrated in FIG. 6, rotary motion is first transmitted from the drive shaft 4 of the motor 2 directly to the drive shaft 5. Due to the engagement of the bell-shaped gear 23 of the drive shaft 5 with the crown gear 24 of the drive shaft 46, the rotary motion is thus transmitted to the first drive shaft section 46 of the second drive shaft 6. In view of the size relationship of the gears 23 and 24, a stepping-up of the motor speed in the ratio of 1:2.1 is obtained. By means of the gear pairing 47 and 49, as already mentioned an additional step-up in the ratio of 1:1.5 is achieved. A further, however, a smaller step-up in the ratio of 1:1.3 is achieved in the head housing 8 by means of the relationship of the gear 50 to the gear 51. Thus, in the arrangement illustrated in FIG. 6, in bold lines, a total step-up ratio of 1:4.1 is obtained.

As a result of the subdivision of the second drive shaft 6 into the two sections 46 and 48, it is possible to also obtain a step-down in the drive ratio using the same drive shaft part in a reverse order while retaining the gear pairing 47 and 49. For example, by reversing the position of the housing formed by the shank 41, the gear 50, which was previously engaged with the gear 51, will become engaged with the smaller crown gear 45 of the first drive shaft 5 as illustrated in broken lines. Also, the gear 24 will engage with the gear 51 on the drive shaft 7. Although the gear meshing of the gears 47 and 49 is retained, it is in the reverse order so that a step-down will occur therebetween. Thus, by utilizing a connection having the crown gear 50 of the shaft 48, a 1:1 drive ratio is obtained. In this arrangement a step down will occur due to the relationship between the gears 47 and 49.

The two drive shaft sections 46 and 48 can be advantageously designed in such a manner and arranged in the head part 9 so that they can be arranged in either one of the two arrangements completely with their bearings or in the alternative can be built as a unit which can be assembled in either one of the two positions. Thus, a gear pairing can also be formed in which the gear tooth relationship between the two drive shafts 46 and 48 is interchanged and the drive gears are reversed and arranged in a reverse sequence. For example, either a gear pairing 23/24; 49/47; and 50/51 or a gear pairing 45/50; 47/49; and 24/51. Due to this flexibility of arranging the gears and shafts, the number of drive shaft parts to be fabricated can be reduced by means of the above described interchangeability.

The sleeve 18 is axially fixed in the grip part 10, which covers the drive shaft sections 5 and also covers the drive shaft section 6 over a large part, by means of the threaded ring 28. To this end, both the grip part 10 as well as the sleeve 18 are provided with a section 53 serving as a positioning guide. The threaded ring 28 contains the groove 17 which is adapted to receive the spring washer 16 and the spring washer 16 is inserted radially resiliently in a groove 54 of the sleeve 14. When the sleeves 10 and 18 are connected to one another by means of the threaded ring 28, and the combination is axially placed on the sleeve 14, the spring washer 16 snaps into the spring washer groove 17 of the threaded ring 28. By means of overcoming a specific axial tension or force, the grip sleeve 10 with the part secured thereto can then be removed from the sleeve 14. The spacing of the engagement between the gear pairs such as 23 and 24 or respectively 45, 50 can also be adjusted by use of the threaded ring 28.

The sleeve 14 is removably secured in the socket 13 by catch means 15, which is mounted on the projection 12 of the housing for the drive part 1. The catch means 15 contains three balls 56 which are inserted in circumferentially spaced radial bores 55 of the projection 12 and the balls 56 are engaged in recesses 57 of the sleeve 14. The balls 56 are pressed radially inwardly into the recesses 57 by means of a retention ring 58. The retention ring 58 contains a first snap ring groove 59 adapted to the ball surface and a second snap ring groove 60 adapted to the surface of the spring washer 16. The snap ring groove 60 serves for the indissolvable support of the retention ring 58 when the sleeve 18 is removed. By means of axially displacing the retention ring 58 towards the right i.e., towards the head part 9, the groove 60 of the retention ring 58 can thus be placed over the spring washer 16. In this position, the balls 56 can move radially outward, but, however, only up to a detents 61 which are located to loosely retain the ball in each radial bore 55. This detent is dimensioned in such a manner that the sleeve 14 can be axially removed from the sleeve 12.

In the disclosed sample embodiments, the axis of the two drive shaft sections 46 and 48 lie parallel to one another, however, it can also be advantageous to seat the drive shafts in such a manner that their axes intersect at an angle and the teeth of the gear such as 47 and 49 will be designed similar to the teeth of the gears such as 23 and 24. In such a situation, the entire counterbend angle, i.e., the angle which is formed between the motor axis and the axis of the drive shaft section 48 can be increased.

Although various minor modifications may be suggested by those versed in the art, it should be understood that I wish to embody within the scope of the patent granted hereon, all such modifications as reasonably and properly come within the scope of my contribution to the art.

I claim:

1. In a dental handpiece having a drive part with a drive shaft extending in a projection, a head part with a head housing containing socket means for supporting a tool for rotation and having a neck extending therefrom, and a grip part connected to the head part and being removably supported on the projection of said drive part so that it can be axially removed therefrom, said grip part having a drive means for transmitting rotational motion from the drive shaft of the drive part to the socket means, said handpiece having at least one cooling agent line formed of sections in said parts with two of said cooling agent line sections being connected to one another by means of a rotatable connection consisting of an annular channel with annular sealing rings in one said parts, and an opening in the other of said parts in communication with said channel in said other part and being rotatable therearound, the improvements comprising a first drive shaft having means at one end to form a direct coupling with the drive shaft of the drive part and having two coaxially arranged gears of a different number of teeth disposed on the other end, said first drive shaft being supported for rotation in a first sleeve which forms one of the two parts of the rotatable connection and carries one of the coolant agent line sections, a second sleeve forming the other part of the rotatable connection being arranged concentrically on the first sleeve and having cooling line sections for conducting fluid from said connection to the head section, said first sleeve having first means coacting with the drive part for detachably connecting the first sleeve on the projection of said drive part without any rotation therebetween, said first sleeve and second sleeve having second means for releasably securing the second sleeve concentrically on the first sleeve for rotation thereon without any axial displacement, said grip part being formed by said first and second sleeves and an outer sleeve covering supported thereon; said sleeve covering having means for releasably receiving the neck of the housing of the head part, said neck having support means for supporting a second drive shaft in the neck, said second drive shaft having a gear at each end with the gear at one end engaged with a gear of the socket means, said support means for the second drive shaft supporting the second drive shaft with the gear at the other end engaged with one of said two coaxial gears of the first drive shaft section, so that by replacing the head part with another head part having its drive shaft supported with the gear at the other end engaged with the other of said coaxial gears, the gear ratio between the connection of the first drive shaft and the drive shaft of the head part can be changed.

2. In a dental handpiece according to claim 1, wherein said first means includes at least one recess on an outer surface of said first sleeve, a ball for each of said recesses, a radial bore in said projection of said drive part for each ball, and means for holding said ball in its bores against said recess to form the releasable connection of said first sleeve with said projection.

3. In a dental handpiece according to claim 2, wherein the second means includes a resilient ring carried on said first sleeve and an annular groove in said second sleeve, said means for holding said ball of said first means including means for holding said resilient ring in a retracted position to enable assembly of said second sleeve on said first sleeve.

4. In a dental handpiece according to claim 3, wherein said means for holding comprises a ring member telescopically received on said projection and having a first groove for said balls when holding said balls in said recesses and a second axially spaced groove for engaging said resilient ring as said ring member is displaced onto said first sleeve.

5. A dental handpiece comprising a drive part with a drive shaft extending in a projection; a head part with a head housing containing socket means for supporting a tool for rotation and having a neck extending from said housing; a grip part comprising a first sleeve rotatably supporting a first drive shaft having means at one end to form a direct coupling with the drive shaft of the drive part and having coaxially arranged gears of a different number of teeth being disposed on the other end, a second sleeve being arranged concentrically on the first sleeve and an outer sleeve supported thereon, said sleeve covering having means for releasably receiving the neck of the head part; first means for detachably connecting the first sleeve in the projection of said drive part without any axial displacement and rotation therebetween, said first means removably connecting the grip part on the drive part with the one end of the first drive shaft being coupled to the drive shaft of the drive part; and second means for releasably securing the second sleeve concentrically onto the first sleeve for rotation therewith without any axial displacement, said handpiece having at least one cooling agent line being formed by sections in said drive part, first sleeve and second sleeve and head part extending from said drive part through said grip part to a nozzle adjacent the socket means of the head part, said first and second sleeves having means forming a rotatable connection between the sections in the first and second sleeves including an annular channel with an annular seal ring in one of said first and second sleeves and an opening in the other of said first and second sleeves in communication with the channel of the one sleeve, said neck of the head part having the support means for supporting a second drive shaft for rotation in said neck, said second drive shaft having a gear at each end with the gear at one end engaged with a gear on the socket means in the head housing, said support means for the second drive shaft supporting the second drive shaft with the gear at the other end engaged with one of the two coaxial gears of the first drive shaft section, said first and second drive shafts forming drive means for transmitting rotational motion from the drive shaft of the drive part to the socket means so that by replacing the head part with another head part having its drive shaft supported with the gear at the other end engaged with the other of said coaxial gears, the gear ratio between the connection for the first drive shaft and the second drive shaft can be changed.

6. A dental handpiece according to claim 5, wherein said first means includes at least one circular recess on an outer surface of said first sleeve, a ball for each of said recesses, a radial bore in said projection of said drive part for each ball, and means for holding said ball in its bores against said recess to form the releasable connection of said first sleeve with said projection.

7. A dental handpiece according to claim 6, wherein the second means includes a resilient ring carried on said first sleeve and an annular groove in said second sleeve, said means for holding said ball of said first means including means for holding said resilient ring in a retracted position to enable assembly of said second sleeve on said first sleeve.

8. A dental handpiece according to claim 7, wherein said means for holding comprises a ring member telescopically received on said projection and having a first groove for engaging the balls when holding said balls in said recesses and a second axially spaced groove for engaging said resilient ring as said ring member is displaced onto said first sleeve.

* * * * *